US006770054B1

(12) United States Patent
Smolyarov et al.

(10) Patent No.: US 6,770,054 B1
(45) Date of Patent: Aug. 3, 2004

(54) INJECTOR ASSEMBLY WITH DRIVING MEANS AND LOCKING MEANS

(75) Inventors: Boris V. Smolyarov, Voronezh (RU); Victor T. Rogatchev, Voronezh (RU)

(73) Assignee: Felton International, Inc., Lenexa, KS (US)

( * ) Notice: Subject to any disclaimer, the term of this patent is extended or adjusted under 35 U.S.C. 154(b) by 42 days.

(21) Appl. No.: 09/717,548

(22) Filed: Nov. 21, 2000

Related U.S. Application Data

(63) Continuation-in-part of application No. 09/685,633, filed on Oct. 10, 2000, now Pat. No. 6,626,871, and a continuation-in-part of application No. 09/685,499, filed on Oct. 10, 2000.

(30) Foreign Application Priority Data

Nov. 23, 1999 (RU) .......................................... 99124267

(51) Int. Cl.[7] .............................................. A61M 37/00
(52) U.S. Cl. ...................................... 604/140; 604/131
(58) Field of Search .............................. 604/187, 140, 604/70, 198, 72, 131, 68, 207, 69

(56) References Cited

U.S. PATENT DOCUMENTS

| | | | |
|---|---|---|---|
| 2,821,981 A | 2/1958 | Ziherl et al. |
| 3,057,349 A | 10/1962 | Ismach |
| 3,202,151 A | 8/1965 | Kath |
| 3,292,622 A | 12/1966 | Banker |
| 3,490,451 A | 1/1970 | Yahner |
| 3,515,130 A | 6/1970 | Tsujino |
| 3,518,990 A | 7/1970 | Banker |
| 3,526,225 A | 9/1970 | Isobe |
| 3,561,443 A | 2/1971 | Banker |
| 3,788,315 A | 1/1974 | Laurens |
| 3,859,996 A | 1/1975 | Mizzy et al. |
| 3,933,155 A | 1/1976 | Johnston |
| 4,007,739 A | 2/1977 | Bron |
| 4,059,107 A | 11/1977 | Iriguchi et al. |
| D248,568 S | 7/1978 | Ismach |
| 4,103,684 A | 8/1978 | Ismach |
| 4,124,024 A | 11/1978 | Schwebel et al. |
| 4,165,739 A | 8/1979 | Doherty et al. |
| 4,266,541 A | 5/1981 | Landau |
| 4,400,171 A | 8/1983 | Dettbarn et al. |
| 4,403,986 A | 9/1983 | Dettbarn et al. |
| 4,592,742 A | 6/1986 | Landau |
| 4,596,556 A | 6/1986 | Morrow et al. |
| 4,642,095 A | 2/1987 | Dettbarn et al. |
| 4,722,728 A | 2/1988 | Dixon |
| 4,850,967 A | 7/1989 | Cosmai |
| 4,874,367 A | 10/1989 | Edwards |
| 4,913,699 A | 4/1990 | Parsons |
| 5,009,637 A | 4/1991 | Newman et al. |
| 5,024,656 A | 6/1991 | Gasaway et al. |
| 5,049,125 A | 9/1991 | Accaries et al. |
| 5,062,830 A | 11/1991 | Dunlap |
| 5,063,905 A | 11/1991 | Farrell |
| 5,064,413 A | 11/1991 | McKinnon et al. |
| 5,176,645 A | 1/1993 | Guerrero |
| 5,256,142 A | 10/1993 | Colavecchio |
| 5,279,608 A | 1/1994 | Cherif Cheikh |
| 5,312,335 A | 5/1994 | McKinnon et al. |
| 5,354,286 A | 10/1994 | Mesa et al. |
| 5,383,851 A | 1/1995 | McKinnon et al. |
| 5,399,163 A | 3/1995 | Peterson et al. |
| 5,456,388 A | 10/1995 | Honstein et al. |
| 5,501,666 A | 3/1996 | Spielberg |
| 5,503,627 A | 4/1996 | McKinnon et al. |
| 5,512,043 A | 4/1996 | Verkaart |
| 5,520,639 A | 5/1996 | Peterson et al. |
| 5,536,249 A | 7/1996 | Castellano et al. |
| 5,569,189 A | 10/1996 | Parsons |
| 5,569,190 A | 10/1996 | D'Antonio |
| 5,569,209 A | 10/1996 | Roitman |
| 5,573,767 A | 11/1996 | Dufour et al. |
| 5,584,182 A | 12/1996 | Althaus et al. |
| 5,593,390 A | 1/1997 | Castellano et al. |
| 5,599,302 A | 2/1997 | Lilley et al. |

(List continued on next page.)

FOREIGN PATENT DOCUMENTS

| | | |
|---|---|---|
| EP | 0347190 | 12/1989 |
| EP | 0526772 | 2/1993 |
| EP | 0776224 | 6/1997 |
| EP | 0788386 | 8/1997 |
| EP | 0799064 | 10/1997 |
| EP | 0888790 | 1/1999 |
| EP | 0888791 | 1/1999 |
| EP | 0951917 | 10/1999 |
| FR | 2629348 | 10/1989 |
| FR | 2641190 | 7/1990 |
| RO | 0108150 | 2/1994 |

(List continued on next page.)

OTHER PUBLICATIONS

*Cool. Click: A Needle–Free Device For Growth Hormone Delivery, The Medical Letter*, vol. 43, No. 1095, pp. 2–3 (Jan. 8, 2001).

Figge, et al., *Anatomic Evaluation of a Jet Injection Instrument Designed to Minimize Pain and Inconvenience of Parental Therapy, The American Practitioner*, vol. 3, No. 4, pp. 197–206 (Dec. 1948).

(List continued on next page.)

*Primary Examiner*—Manuel Mendez
(74) *Attorney, Agent, or Firm*—Mayer Brown Rowe & Maw LLP; Joseph A. Mahoney; Christine M. Rebman (57) ABSTRACT

Disclosed is an injector assembly having driving means for injecting a substance into a subject and locking means for retaining the driving means until a predetermined amount of pressure builds in a cavity near the driving means.

36 Claims, 5 Drawing Sheets

U.S. PATENT DOCUMENTS

| | | | |
|---|---|---|---|
| 5,599,309 | A | 2/1997 | Marshall et al. |
| 5,618,268 | A | 4/1997 | Raines et al. |
| 5,620,434 | A | 4/1997 | Brony |
| 5,643,211 | A | 7/1997 | Sadowski et al. |
| 5,697,917 | A | 12/1997 | Sadowski et al. |
| 5,704,911 | A | 1/1998 | Parsons |
| 5,713,875 | A | 2/1998 | Tanner, II |
| 5,716,346 | A | 2/1998 | Farris |
| 5,722,953 | A | 3/1998 | Schiff et al. |
| 5,728,074 | A | 3/1998 | Castellano et al. |
| 5,730,723 | A | 3/1998 | Castellano et al. |
| 5,746,714 | A | 5/1998 | Salo et al. |
| 5,746,733 | A | 5/1998 | Capaccio et al. |
| 5,755,696 | A | 5/1998 | Caizza |
| 5,769,138 | A | 6/1998 | Sadowski et al. |
| 5,776,125 | A | 7/1998 | Dudar et al. |
| 5,782,802 | A | 7/1998 | Landau |
| 5,785,688 | A | 7/1998 | Joshi et al. |
| 5,788,675 | A | 8/1998 | Mayer |
| 5,800,388 | A | 9/1998 | Schiff et al. |
| 5,803,078 | A | 9/1998 | Brauner |
| 5,807,374 | A | 9/1998 | Caizza et al. |
| 5,814,024 | A | 9/1998 | Thomson et al. |
| 5,817,082 | A | 10/1998 | Niedospial, Jr. et al. |
| 5,820,601 | A | 10/1998 | Mayer |
| 5,820,621 | A | 10/1998 | Yale et al. |
| 5,827,244 | A | 10/1998 | Boettger |
| 5,830,193 | A | 11/1998 | Higashikawa |
| 5,832,971 | A | 11/1998 | Yale et al. |
| 5,833,213 | A | 11/1998 | Ryan |
| 5,833,668 | A | 11/1998 | Aguilar |
| 5,833,674 | A | 11/1998 | Turnbull et al. |
| 5,836,911 | A | 11/1998 | Marzynski et al. |
| 5,836,923 | A | 11/1998 | Mayer |
| 5,839,715 | A | 11/1998 | Leinsing |
| 5,840,061 | A | 11/1998 | Menne et al. |
| 5,840,062 | A | 11/1998 | Gumaste et al. |
| 5,846,233 | A | 12/1998 | Lilley et al. |
| 5,851,198 | A | 12/1998 | Castellano et al. |
| 5,858,001 | A | 1/1999 | Tsals et al. |
| 5,860,961 | A | 1/1999 | Gettig |
| 5,860,962 | A | 1/1999 | Lewandowski et al. |
| 5,865,795 | A | * 2/1999 | Schiff et al. .................. 604/70 |
| 5,865,796 | A | 2/1999 | McCabe |
| 5,922,685 | A | 7/1999 | Rakhmilevich et al. |
| 6,053,889 | A | 4/2000 | Heinzen et al. |
| 6,056,716 | A | * 5/2000 | D'Antonio et al. ............ 604/68 |
| 6,080,130 | A | 6/2000 | Castellano |
| 6,083,197 | A | 7/2000 | Umbaugh |
| 6,096,002 | A | 8/2000 | Landau |
| 6,102,896 | A | 8/2000 | Roser |
| 6,135,979 | A | 10/2000 | Weston |
| 6,241,709 | B1 | 6/2001 | Bechtold et al. |
| 6,258,062 | B1 | 7/2001 | Thielen et al. |
| 2002/0004639 | A1 | 1/2002 | Willis et al. |
| 2002/0035348 | A1 | 3/2002 | Hjertman |

FOREIGN PATENT DOCUMENTS

| | | |
|---|---|---|
| RO | 0106078 | 2/1996 |
| RU | 257697 | 11/1968 |
| RU | 373005 | 3/1971 |
| RU | 476876 | 10/1977 |
| RU | 718111 | 2/1980 |
| RU | 1279636 | 12/1986 |
| RU | 2008932 C1 | 1/1990 |
| RU | 2108117 | 1/1991 |
| RU | 2008932 | 3/1994 |
| RU | 2108117 | 4/1998 |
| SU | 0257697 | 11/1969 |
| SU | 0373005 | 3/1973 |
| SU | 0573160 | 11/1977 |
| SU | 0718111 | 2/1980 |
| SU | 0793580 | 1/1981 |
| SU | 0835448 | 6/1981 |
| SU | 0835449 | 6/1981 |
| SU | 0957914 | 9/1982 |
| SU | 1107874 | 8/1984 |
| SU | 1144705 | 3/1985 |
| SU | 1168261 | 7/1985 |
| SU | 1219093 | 3/1986 |
| SU | 1230600 | 5/1986 |
| SU | 1271524 | 11/1986 |
| SU | 1279636 | 12/1986 |
| SU | 1560201 | 4/1990 |
| SU | 1839093 | 12/1993 |
| WO | 9734652 | 9/1997 |
| WO | 9813470 | 4/1998 |
| WO | 9901168 | 1/1999 |
| WO | 9901169 | 1/1999 |
| WO | 9903529 | 1/1999 |

OTHER PUBLICATIONS

Brochure on Agro–Jet: Needle–Less Jet Injector by M.I.T.
Description and Operating Instuctions for Hydraulic Needleless Injector by V/O Medexport in Moscow.
Dimache, et al., *A Clinical, Epidemiological and Laboratory Study on Avoiding the Risk of Transmitting Viral Hepatitis During Vaccinations with the Dermojet Protected by an Anticontaminant Disposable Device*, Vaccine, vol. 15, No. 8, pp. 1010–1013 (1997).
Jet Gun Injection Transmission: *A Clinical, Epidemiological and Laboratory Study on Avoiding the Risk of Transmitting Viral Hepatitis During Vaccinations with the Dermojet Protected by an Anticontaminant Disposable Device*, American Journal of Infection Control, vol. 26, No. 4, pp. 442–445 (Aug. 1998).

* cited by examiner

INJECTOR ASSEMBLY WITH DRIVING MEANS AND LOCKING MEANS

CROSS REFERENCE OF RELATED APPLICATIONS

This application claims priority to, and benefit from, Russian Patent Application 99124267, filed Nov. 23, 1999, now issued as Russian Patent No. 2155015; U.S. patent application Ser. No. 09/685,633, filed Oct. 10, 2000; and U.S. patent application Ser. No. 09/685,499, filed Oct. 10, 2000. The contents of all such documents are incorporated herein by reference to the extent permitted by law.

TECHNICAL FIELD OF THE INVENTION

The invention relates to an injector device having a locking means that prevents a driving means from expelling a substance before a predetermined amount of pressure has been achieved within the device.

BACKGROUND OF THE INVENTION

The traditional needleless injectors include the basic design: a housing with an inner power unit, a medication unit, and a nozzle. The function of the power unit is to pump the medication into an under-plunger cavity of the medication unit chamber and to expel the medication through the nozzle.

Some needleless injectors are powered by a pneumatic drive. These injectors may include an injection chamber having a piston and nozzle, a pneumatic cylinder having a power pneumatic piston, a gas distribution unit, a pipeline for the supply of compressed air into the pneumatic cylinder, and an exhaust for the release of compressed air into the atmosphere. Significant disadvantages prevail in this type of injector. First, the time for increasing a pressure to drive the pneumatic piston is relatively long. A dead volume in the injector cavity requires time to fill and achieve the required pressure. This initially allows jet formation with insufficient kinetic energy to properly pierce the subject's skin and results in poor overall injection quality both in terms of the depth (transdermal, subcutaneous, or intramuscular) and the amount of medication delivered. To this end, a device that prevents the driving means from expelling the medicine before the required amount of pressure has built is needed.

Another disadvantage of the described needleless injector is the need to return the power piston and other moveable parts to their initial position. Typically, this is accomplished using a mechanical spring. Mechanical springs increase the dimensions and mass of the jet injector and are a common mode of failure.

Accordingly, there is a need in the art of needleless injector devices to solve the problem of early injection. More particularly, there is a need for an injector that increases the quality of an injection, decreases the loss of medicine on the skin's surface, and decreases the dimensions and mass of a jet injector.

SUMMARY OF THE INVENTION

The foregoing problems are solved and a technical advance is achieved by the present invention. Disclosed is an injector assembly having driving means for injecting a substance into a subject and locking means for retaining the driving means. More particularly, the present invention relates to an injector assembly comprising a piston assembly having a piston and a spring, a lock assembly having at least one roller, at least one roller retainer, and an annular groove, the lock assembly configured to engage the piston assembly, an injection chamber, wherein the piston assembly is configured to drive a substance out of the injection chamber, and a pneumatic pressure unit detachably attached to the piston assembly by at least one path.

DETAILED DESCRIPTION OF THE INVENTION

Figure 1:
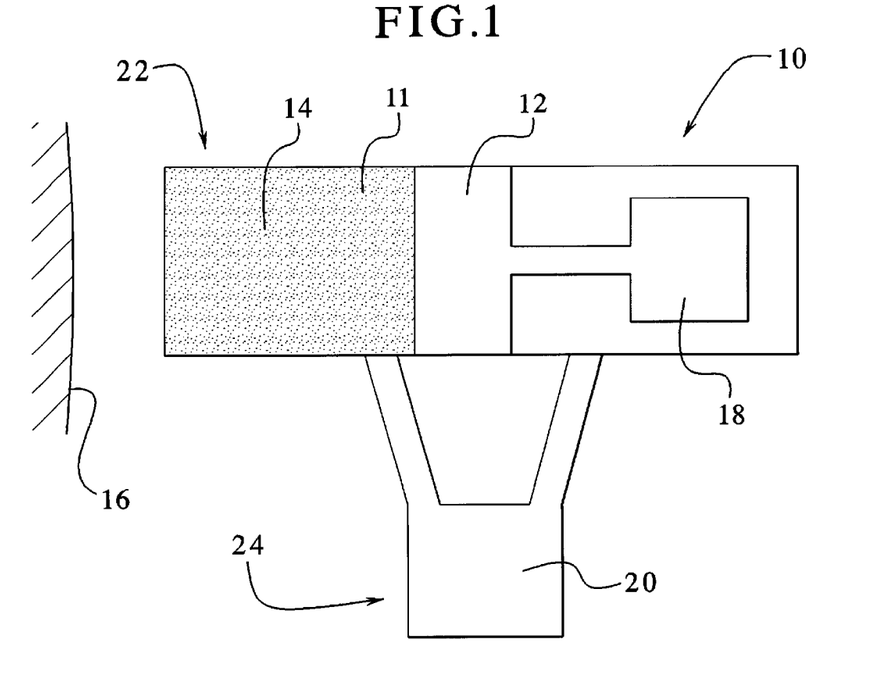
FIG. 1 is a cross-sectional view of one embodiment of the invention.

FIG. 1 depicts an injector assembly 10 having an injection chamber 11, a driving means 12 for injecting a substance 14 into a subject 16, and a locking means 18 for retaining the driving means 12. Injector assembly 10 may further include a means for releasing 20 the driving means 12 from the locking means 18. Injector assembly 10 may comprise one or more components housing the driving means 12, the locking means 18, and the means for releasing 20. In one embodiment, the driving means 12 and the locking means 18 are located in a first component 22 and the means for releasing 20 is located in a second component 24. The term "located in" encompasses all variations of the term, including but not limited to, being partially or completely located in a specified area.

Many types of driving means 12 may be employed in the present invention. The driving means 12 can include those means known in the art and can further include, but is not limited to, pistons, gears, rods, springs, work gears, screws, electromagnets, optical components, and jacks. The driving means 12 may also include various driving mechanisms, such as pneumatics, hydraulics, or manual drives. In addition, the driving means 12 may include phase change materials or other shape memory materials, such as those materials that change size or; shape due to temperature application. One such material is Nitinol, which allows for size or shape transformation in its austenite and martensite states. Accordingly, the driving means 12 is meant to include not only the structures described herein, but also, any acts or materials described herein, and also include any equivalent structures, equivalent acts, or equivalent materials; or structural equivalents, act equivalents, or material equivalents, to those described herein.

Similarly, many types of locking means 18 may be employed in the present invention. The locking means 18 can include those means known in the art and can further include, but is not limited to, tongue and groove, rollers and retainers, notches, screw types with threading, electromagnetic devices, and restricto-magnetic devices. Accordingly, the locking means 18 is meant to include not only the structures described herein, but also, any acts or materials described herein, and also include any equivalent structures, equivalent acts, or equivalent materials; or structural equivalents, act equivalents, or material equivalents, to those described herein.

Figure 2:
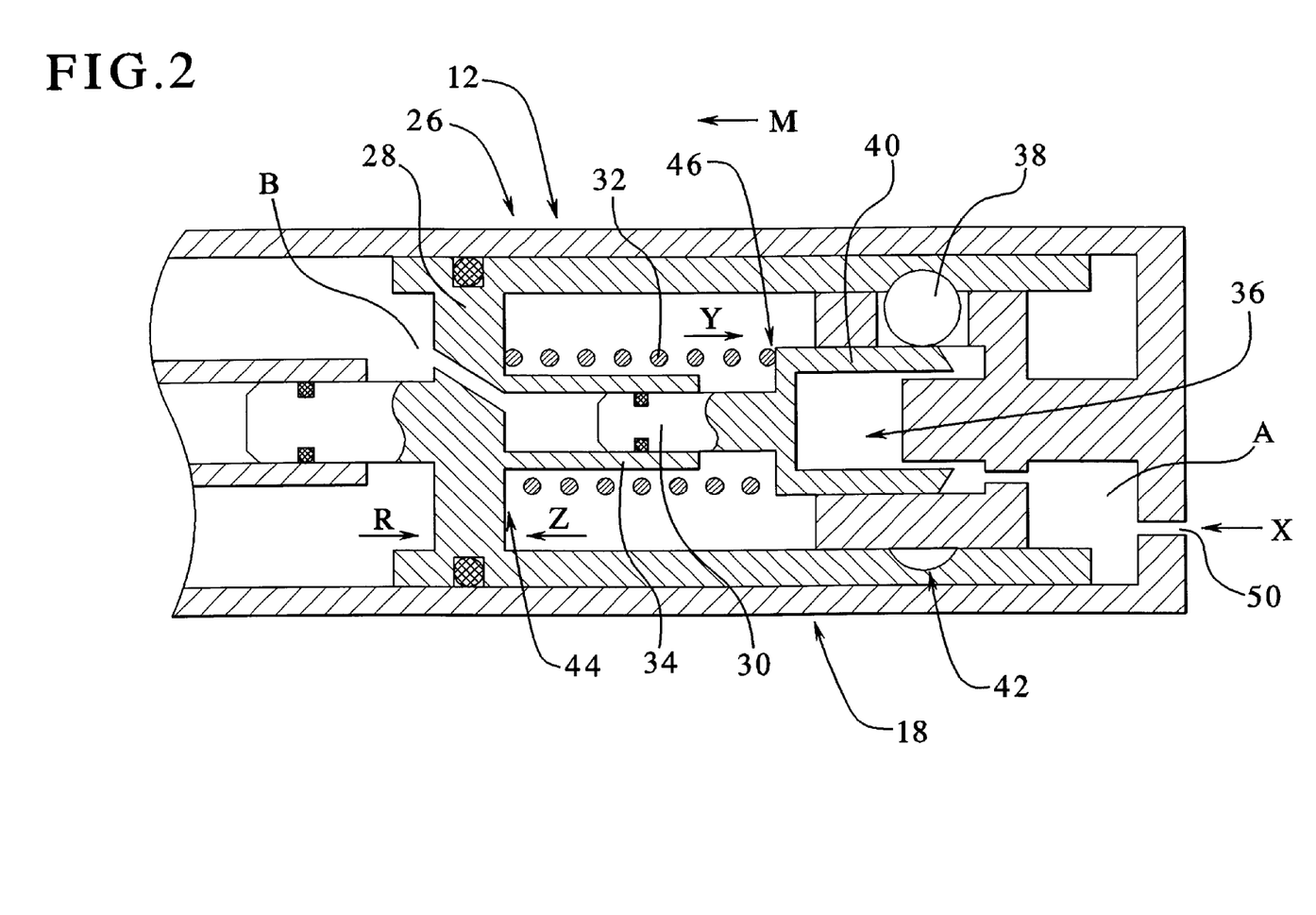
FIG. 2 is a cross-sectional view demonstrating the driving assembly and lock assembly of the present invention.
Figure 4:
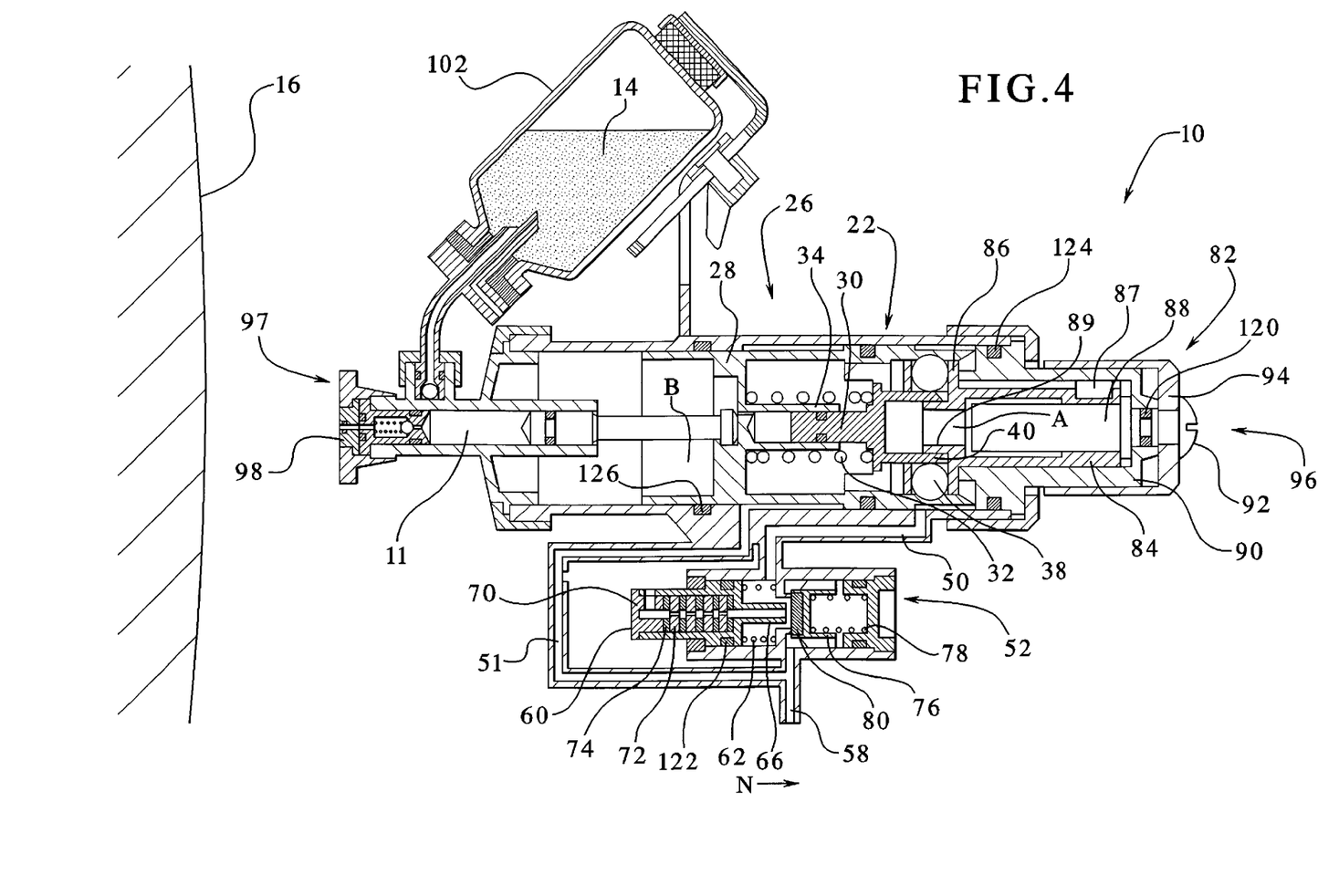
FIG. 4 is a cross-sectional view of another embodiment of the present invention, particularly the dosing unit.

FIG. 2 depicts another embodiment of the invention. The driving means 12 comprises a driving assembly 26 having a piston 28, a piston rod 30, and a spring 32. The piston rod 30 glides through a cylinder 34 formed within the piston 28. The locking means 18 comprises a lock assembly 36 having at least one roller 38, at least one roller retainer 40, and annular groove 42. Annular groove 42 forms an internal toroid surface inside piston 28 and retains piston 28 in a locked position until the injection takes place. The embodiment in FIG. 2 depicts a lock assembly 36 having one roller 38, one roller retainer 40, and annular groove 42. It is to be understood by one skilled in the art that only one roller 38 and one roller retainer 40 is necessary to carry out the purpose of the invention; however, the lock assembly 36 may comprise one or more rollers 38 and roller retainers 40, as depicted in FIG. 4. The spring 32 of driving assembly 26 is situated between the piston 28 and the roller retainer 40. A proximal end 44 of the spring 32 abuts piston the 28 and a distal end 46 of the spring 32 abuts the roller retainer 40 when the driving assembly 26 is in a locked position. The piston rod 30 is manufactured jointly with the roller retainer 40. The roller retainer 40 holds and releases the roller 38 in the annular groove 42 of the piston 28.

Any type of means for releasing 20 may be employed in the invention including those means known in the art and further including, but not limited to, pneumatic power units, hydraulic power units, manual drives, cable connections, electro-mechanical devices, computer sources, or any combination thereof. Accordingly, the means for releasing 20 is meant to include not only the structures described herein, but also, any acts or materials described herein, and also include any equivalent structures, equivalent acts, or equivalent materials; or structural equivalents, act equivalents, or material equivalents, to those described herein.

In one embodiment, as shown in FIG. 4, the means for releasing 20 the driving means 12 comprises a power unit 48 and at least one path 50. At least one path 50 detachably attaches power unit 48 to first component 22 to provide fluid communication between the power unit 48 and the first component 22. More than one path may provide communication between the power unit 48 and the first component 22. The power unit 48 communicates with the first component 22 by applying a pressure to driving assembly 26. The power unit 48 may be powered by any type or number of power sources including, but not limited to pneumatic pressure, hydraulic pressure, manual drives, or any combination thereof.

Figure 3A:
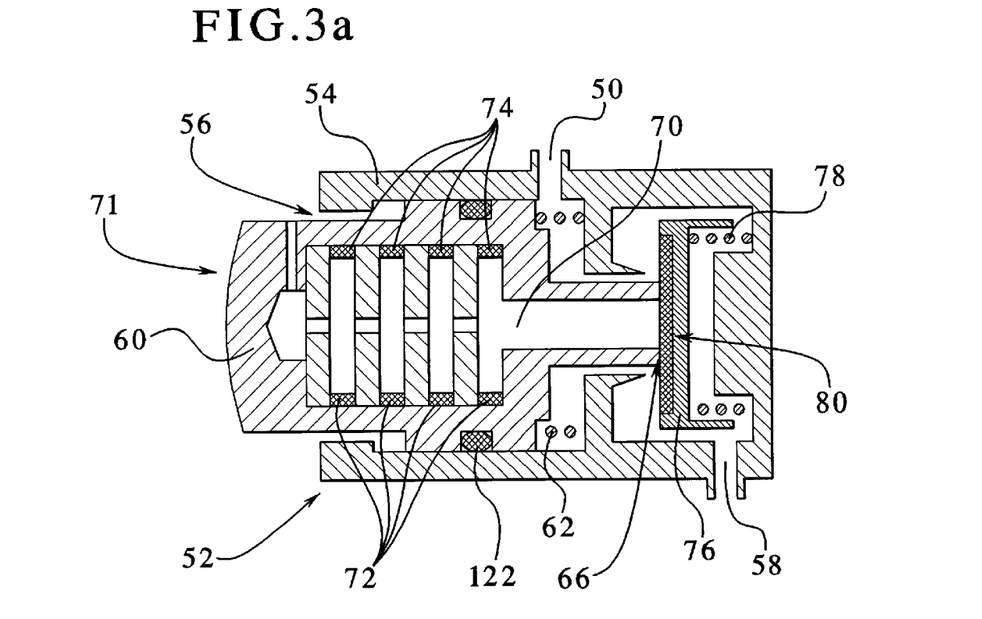
FIG. 3a is a cross-sectional view demonstrating a pneumatic power unit of the present invention in a position prior to injection.
Figure 3B:
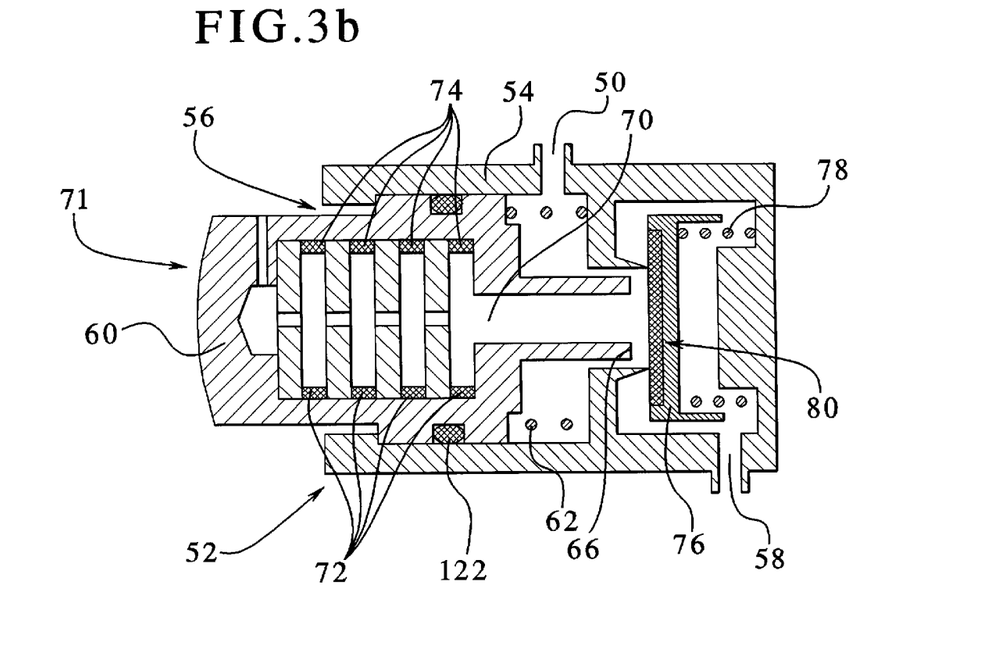
FIG. 3b is a cross-sectional view demonstrating a pneumatic power unit of the present invention in a position after injection.

FIGS. 3a and 3b depict a pneumatic pressure unit 52. Pneumatic power unit 52 modulates pneumatic energy supplied by power unit 48. The pneumatic pressure unit 52 comprises a body 54 having a proximal end bore 56 and a distal end bore 58. A button 60 seats within the proximal end bore 56. The button 60 activates the pneumatic pressure unit 52 to release pressure in the form of compressed air. The button 60 is biased by a button spring 62 and is sealed by a ring 122. In one embodiment, the button 60 is hollow and comprises an inner end 66 and a channel 70. The channel 70 connects to the atmosphere outside of the injector assembly 10. The channel 70 serves as an exhaust assembly 71 further having several gaskets 74 separated by orifice plates 72 to suppress noise produced by the pneumatic pressure unit 52 upon injection of the substance 14 (not shown in FIGS. 3a and 3b). Compressed air is supplied through the distal end bore 58. An inlet valve 76 biased by a valve spring 78 controls the destination of the compressed air from distal end bore 58. A sealing element 80 seats between the inner end 66 of the button 60 and the inlet valve 76 and moves with the inlet valve 76 upon compression of the button spring 62 or release of the valve spring 78.

In one embodiment, depicted in FIG. 4, pneumatic power unit 52 communicates with the first component 22 through the path 50 and the path 51. The path 50 supplies pressure to a cavity A near the piston rod 30. The inlet valve 76 controls the supply of compressed air to the path 50. The path 51 supplies pressure to a cavity B near the piston 28. The distinctions between these two paths and the function of the path 50 and the path 51 are described in more detail below.

FIG. 2 depicts another aspect of the invention. The driving assembly 26 includes a piston 28, a piston rod 30, and a self-biasing mechanism 31. In one embodiment, depicted in FIG. 2, the self-biasing mechanism includes a spring 32. The piston rod 30 glides through a cylinder 34 formed within the piston 28. Further, the lock assembly 36 includes at least one roller 38, at least one roller retainer 40, and annular groove 42. Annular groove 42 forms an internal toroid surface inside piston 28 and retains piston 28 in a locked position until the injection takes place. The embodiment in FIG. 2 depicts a lock assembly 36 having one roller 38, one roller retainer 40, and annular groove 42. It is to be understood by one skilled in the art that only one roller 38 and one roller retainer 40 is necessary to carry out the purpose of the invention; however, the lock assembly 36 may comprise one or more rollers 38 and roller retainers 40, as depicted in FIG. 4. The spring 32 of driving assembly 26 is situated between the piston 28 and the roller retainers 40. A proximal end 44 of the spring 32 abuts piston 28 and a distal end 46 of the spring 32 abuts the roller retainer 40 when the driving assembly 26 is in a locked position. The piston rod 30 is connected to the roller retainer 40. The roller retainer 40 holds and releases the roller 38 in the annular groove 42 of the piston 28.

FIG. 4 depicts another aspect of the invention. Shown is at least one path 50 detachably attaching the power unit 48 to the first component 22 to provide fluid communication between the power unit 48 and the first component 22. More than one path may provide communication between the power unit 48 and the first component 22. The power unit 48 communicates with the first component 22 by applying a pressure to driving assembly 26. The power unit 48 may be powered by any type or number of power sources including, but not limited to pneumatic pressure, hydraulic pressure, manual drives, or any combination thereof.

FIGS. 3a and 3b depict a pneumatic pressure unit 52. Pneumatic power unit 52 modulates pneumatic energy supplied by power unit 48. The pneumatic pressure unit 52 comprises a body 54 having a proximal end bore 56 and a distal end bore 58. A button 60 seats within the proximal end bore 56. The button 60 activates the pneumatic pressure unit 52 to release pressure in the form of compressed air. The button 60 is biased by a button spring 62 and is sealed by a ring 122 to provide a seal. In one embodiment, the button 60 is hollow and comprises an inner end 66 and a channel 70. The channel 70 connects to the atmosphere outside of the injector assembly 10. The channel 70 serves as an exhaust assembly 71 further having several gaskets 74 separated by orifice plates 72 to suppress noise produced by the pneumatic pressure unit 52 upon injection of the substance 14.

Compressed air is supplied through the distal end bore 58. An inlet valve 76 biased by a valve spring 78 controls the destination of compressed air from distal end bore 58. A sealing element 80 seats between the inner end 66 of the button 60 and the inlet valve 76 and moves with the inlet valve 76 upon compression of the button spring 62 or release of the valve spring 78.

In one embodiment, depicted in FIG. 4, the pneumatic power unit 52 communicates with the first component 22 through the path 50 and the path 51. The path 50 supplies pressure in the direction indicated by arrow X to a cavity A near the piston rod 30. The inlet valve 76 controls the supply of compressed air to the path 50. The path 51 supplies pressure in the direction X to a cavity B near the piston 28.

FIG. 4 demonstrates another embodiment of the present invention. Shown is the first component 22 having a dosing unit 82 for adjusting the delivery of a predetermined amount of the substance 14 (FIG. 1). A guiding cylinder 84 seated within the dosing unit 82 includes a separator 86 abutting the rollers 38, a key 87, and a bore 88. In one embodiment, the bore 88 is a threaded bore. The separator 86 includes at least one radial hole, or pocket, (not shown) having a radius of a sufficient size to allow rollers 38 to seat within the separator 86 for maximum holding capacity. Limiter 89 protrudes from separator 86 to prevent the rollers 38 from falling out of the radial holes. The guiding cylinder 84 is movable within a cylindrical wall 90 of injector assembly 10. An adjustment screw 92 fits in the bore 88 to rotate the guiding cylinder 84 within the cylindrical wall 90. In one embodiment, the key 87 insures that the guiding cylinder 84 only moves axially relative to the cylindrical wall 90 as the adjustment screw 92 is rotated. A bushing 94 at a rearward end 96 of injector assembly 10 prevents axial movement of the adjustment screw 92. The bushing 94 guides the adjustment screw 92 to adjust the position of the separator 86 and thereby the amount of the substance 14 to be delivered to the subject 16.

Rings seal the injector assembly 10 at predetermined locations to prevent leakage of the substance 14 or the fluid or gas employed to create pressure, as depicted in FIG. 4 by rings 120, 122, 124, and 126, for example. In one embodiment, rings 120, 122, 124, and 126 are comprised of a polymeric material. In another embodiment, rings 120, 122, 124, and 126 provide a hermetic seal.

Figure 5:
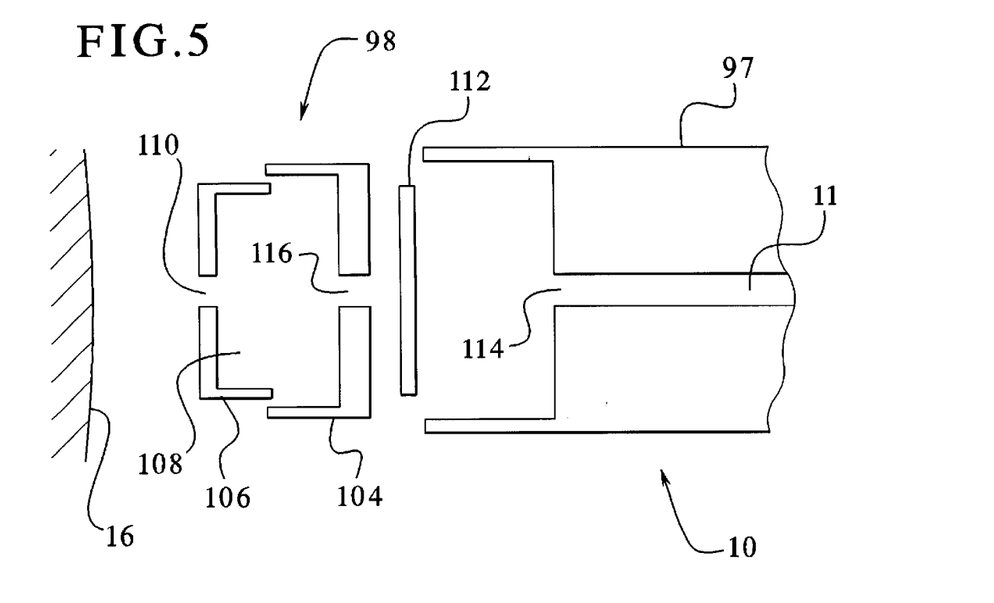
FIG. 5 is a cross-sectional view demonstrating another embodiment of the present invention, particularly the protective cap.
Figure 6:
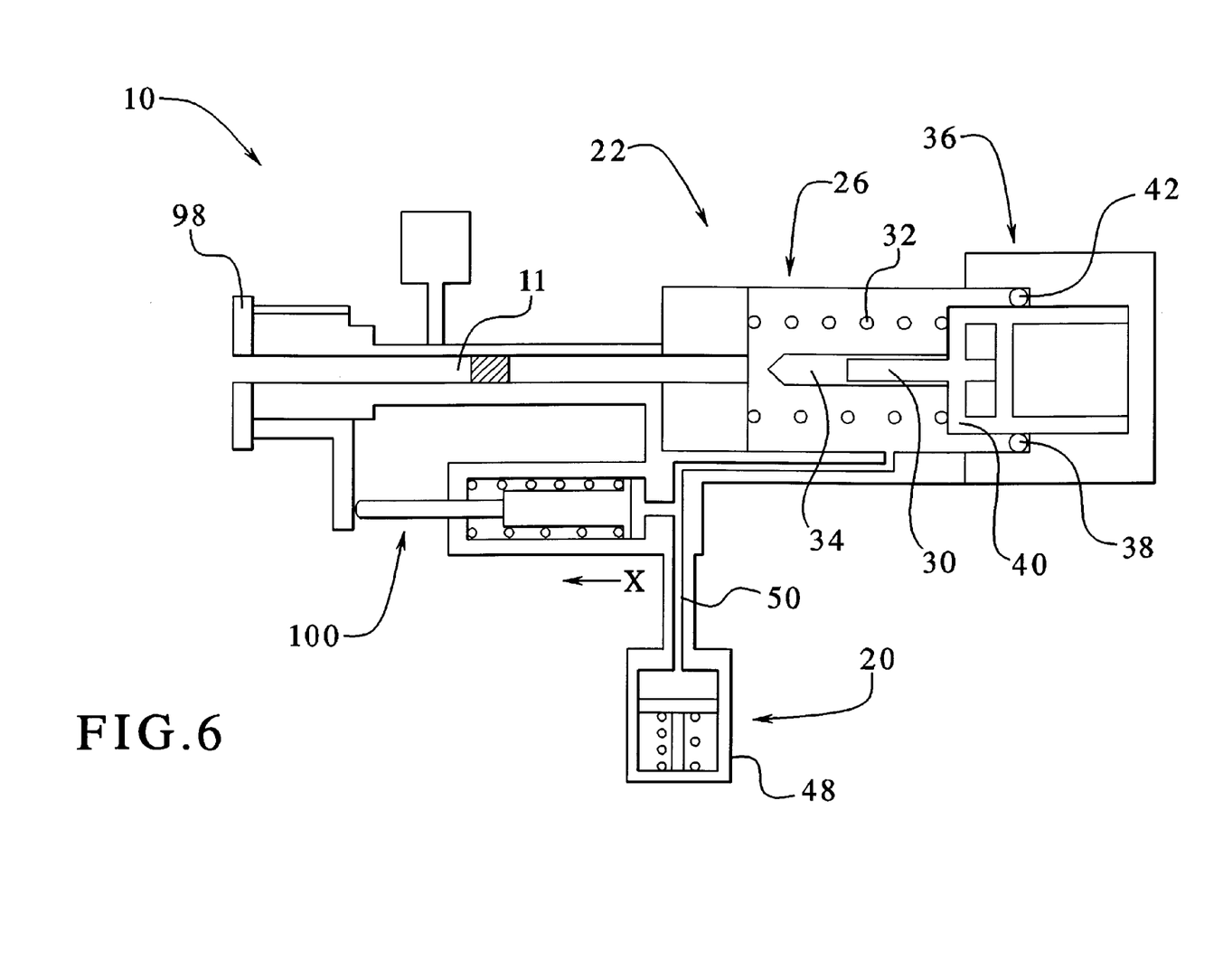
FIG. 6 shows an injector assembly according to one embodiment of the invention.

FIGS. 4 and 5 depict another embodiment of the invention. A protective cap 98 is shown disposed near a front end 97 of injector assembly 10. The protective cap 98 can be detachably attached to the front end 97 using conventional techniques, such as friction fits, bayonet fixing, male-female receptacles, or the like. The protective cap 98 is shown having a baffle 104 and an insert 106. The insert 106 can be adapted to form an insert reservoir 108. Insert 106 also has an insert distal orifice 110. Insert 106 can be adapted to fit with baffle 104 such that the insert 106 provides an additional benefit of back splash protection. As shown in this particular non-limiting embodiment, a protective layer 112 is generally located between, either partially or completely, the baffle 104 and an injector orifice 114. In this configuration, the substance will exit the injector orifice 114, penetrate through the layer 112, and exit through the baffle orifice 116 and insert distal orifice 110 to impact the subject 16. Other embodiments of the protective cap 98 are described in U.S. patent application Ser. No. 09/685,499, filed Oct. 10, 2000, and are incorporated herein by reference.

Referring to FIG. 2, the driving assembly 26 exists within injector assembly 10 in either a resting state or an activated state. The driving assembly 26 is in the resting state when no external pressure in the direction depicted by arrow X is applied to the driving assembly 26. In the resting state, however, a force in the direction Y may be created by the driving assembly 26 and the lock assembly 36. The driving assembly 26 is in the activated state when the external pressure in the direction X is applied to driving assembly 26. When the driving assembly 26 is in the resting state, the driving assembly 26 may be in either a locked position or an unlocked position.

Two resting states and two activated states combine to inject the substance 14 into the subject 16. In the first resting state, the driving assembly 26 is in the locked position and is subject to the spring force in the direction Y. The force in the direction Y is created by the compression of the spring 32 between the piston 28 and the roller retainers 40 when the driving assembly 26 is in the locked position. A first activation state begins when the pressure indicated by the arrow X from the power unit 48 begins to fill cavity A near the piston rod 30. The force in the direction Y is released during the second resting state, which occurs when the pressure in the direction of arrow X reaches a predetermined amount. In the second resting state, no pressures act upon driving assembly 26. A second activated state begins when pressure in the direction R from the pneumatic pressure unit 48 begins to fill cavity B near the piston 28. The force in the direction Z is recreated when the driving assembly 26 enters into the second activated state. Once the pressure indicated by the arrow R reaches a predetermined amount to overcome the force in the direction Z during the second activated state, the driving assembly 26 returns to the first resting state in a locked position. The "predetermined amount of pressure" is defined as the amount of pressure sufficient to overcome the forces indicated by arrows Y and Z created by spring 32. In one embodiment, the predetermined amount of pressure is equal to about 70% of the operation pressure of the compressed gas.

In FIG. 2, the driving assembly 26 rests in the locked position in the first resting state. When the driving assembly 26 is in the locked position, the roller 38 seats in the annular groove 42 of the piston 28. The seating of the roller 38 into groove 42 prevents piston 28 from moving in the direction indicated by arrow M despite the torsion force of spring 32. The driving assembly 26 remains in this locked position of the first resting state until pressure indicated by the arrow X generated from the power unit 48 and supplied through the path 50 builds to the predetermined amount against the piston rod 30 in the cavity A during the first activated state. This occurs when a user presses the button 60 of the pneumatic pressure unit 52, as depicted in FIGS. 3a and 4. When the button 60 is depressed, the inner end 66 pushes against the sealing element 80 and the inlet valve 76, thereby closing channel 70 and opening the path 50 from the distal end bore 58 and releasing compressed air to the cavity A. Referring back to FIG. 2, when the predetermined amount of the pressure indicated by the arrow X is built against the piston rod 30, the roller retainer 40 pushes against the spring 32 in the direction M. As a result, the roller 38 rolls towards the center axis of the injector assembly 10 behind the roller retainer 40 causing the piston 28 to release from the roller 38 and to also move in the direction M under the pressure indicated by the arrow X from the power unit 48 and the force indicated by the arrow Z of the spring 32. The movement of the piston 28 in the M direction causes the substance 14 to propel through and exit the injection chamber 11 into the subject 16.

Referring to FIGS. 3b and 4, when the injection is completed, the button 60 returns to its original released position under the force of the button spring 62. Under the action of the valve spring 78, the inlet valve 76 closes and interrupts the supply of compressed air into the cavity A. Then the inner end 66 opens to the path 50 thereby connecting the cavity A and the channel 70 to release the compressed air to the outside atmosphere. Air from the cavity A and the channel 70 exhausts to the outside atmosphere by passing through several gaskets 74 and orifice plates 72. Thus, the noise produced by the injection and exhaust of compressed air is suppressed.

Referring back to FIG. 2, once the piston 28 reaches the farthest distance in the M direction, the driving assembly 26 is in the unlocked position and enters into the second resting state. At this point, no pressure or force acts upon the driving assembly 26. The driving assembly 26 remains in the second resting state until the power unit 48 supplies the predetermined amount of the pressure indicated by the arrow R. As the compressed air exhausts from the channel 70, the inlet valve 76 and sealing element 80 prevent new compressed air supplied from the distal end bore 58 from travelling through the path 50 to the cavity A. Therefore, the compressed air bypasses through the path 51 to the cavity B. While the pressure indicated by the arrow R builds against the piston 28 in the cavity B during the second activated state, the piston 28 approaches the spring 32. When a predetermined amount of the pressure indicated by the arrow R builds against the piston 28, the spring 32 pushes the roller retainer 40 in the direction N toward the roller 38. Hence the roller retainer 40 pushes the roller 38 away from the center axis to secure the roller 38 into the annular groove 42 of the piston 28. At this point, the driving assembly 26 returns to the locked position of the first resting state.

In one embodiment, depicted in FIG. 4, as the driving assembly 26 travels in the direction N, a vacuum is created in the injection chamber 11. The vacuum draws the substance 14 from a vial 102 into the injection chamber 11 to prepare the injector assembly 10 for another injection. This mechanism and apparatus are described in further detail in U.S. patent application Ser. No. 09/685,633, filed Oct. 10, 2000 and is incorporated herein by reference.

In yet another embodiment of the present invention as illustrated in FIG. 4, the dosage amount of the substance 14 can be adjusted by rotating the bushing 94 and the adjustment screw 92. Rotation of the adjustment screw 92 displaces the separator 86 along a horizontal axis. Displacement of the separator 86 can either increase or decrease the size of the injection chamber 11 by changing the motion length of piston 28. For example, clockwise rotation of the bushing 94 may cause the separator 86 to move towards the front end 97 of the injector assembly 10 thereby decreasing the size of the injection chamber 11; whereas counterclockwise rotation of the bushing 94 may cause the separator 86 to move towards the rearward end 96 of the injection assembly 10, thereby increasing the size of the injection chamber 11.

Further, applicants hereby incorporate herein by reference contemporaneously filed U.S. patent application Ser. No. 09/717,559 entitled "Safety Mechanism To Prevent Accidental Patient Injection and Methods of Same", naming the following inventors, Boris V. Smolyarov, Victor T. Rogatchev, Victor N. Katov, and Nathaniel Leon filed on Nov. 21, 2000.

It should be understood that the foregoing relates only to a limited number of embodiments that have been provided for illustration purposes only. It is intended that the scope of invention is defined by the appended claims and that modifications to the embodiments above may be made that do not depart from the scope of the claims.

We claim:

1. An injector assembly, comprising:
   (a) driving means for injecting a substance into a subject;
   (b) locking means for retaining the driving means; and
   (c) means for releasing the retained driving means from the locking means, wherein the means for releasing comprises a pneumatic power unit and at least one path detachably attaching the power unit to locking means, wherein the locking means is configured to release the driving, means when the pneumatic power unit builds a predetermined amount of pressure in the at least one path.

2. The injector assembly of claim 1, wherein the driving means comprises a piston.

3. The injector assembly of claim 1, wherein the locking means comprises a spring.

4. The injector assembly of claim 1, wherein the locking means comprises at least one roller.

5. The injector assembly of claim 1, wherein the locking means comprises at least one roller retainer.

6. The injector assembly of claim 1, wherein the locking means comprises an annular groove.

7. The injector assembly of claim 1, wherein the locking means comprises a spring, at least one roller, at least one roller retainer, and an annular groove.

8. The injector assembly of claim 1, further comprising a first component.

9. The injector assembly of claim 8, wherein the driving means and the locking means are located in the first component.

10. An injector assembly, comprising:
    (a) a driving assembly; and
    (b) a lock assembly configured to engage the driving assembly, said lock assembly comprising at least one roller, at least one roller retainer, and an annular groove,
    (c) a pneumatic power unit having at least one path detachably attaching the pneumatic power unit to the driving assembly,
        wherein the lock assembly is configured to release the engaged driving assembly when a predetermined amount of pneumatic pressure from the pneumatic power unit builds near the drive assembly.

11. The injector assembly of claim 10, wherein the driving assembly further comprises a piston.

12. The injector assembly of claim 10, wherein the driving assembly further comprises a biasing mechanism.

13. The injector assembly of claim 10, wherein the driving assembly further comprises a piston and a spring.

14. The injector assembly of claim 10, wherein the lock assembly comprises a spring, at least one roller, at least one roller retainer, and an annular groove.

15. The injector assembly of claim 10, wherein the lock assembly is further configured to engage the driving assembly in at least one of a locked position and an unlocked position.

16. The injector assembly of claim 15, wherein the at least one roller retainer is adapted to hold the at least one roller in the annular groove in the locked position.

17. The injector assembly of claim 10, wherein the pneumatic power unit is further adapted to apply the predetermined amount of pressure to the driving assembly.

18. An injector assembly, comprising: (a) a first component, further comprising (i) a piston assembly comprising a piston, (ii) a lock assembly comprising a spring, at least one roller, at least one roller retainer, and an annular groove, the lock assembly configured to engage the piston assembly, and (iii) an injection chamber, wherein the piston assembly is configured to drive a substance out of the injection chamber; and (b) a pneumatic pressure unit detachably attached to the first component by at least one path, wherein the lock assembly is configured to release the engaged piston assembly when a predetermined amount of pressure from the pneumatic pressure unit builds near the first component.

19. The injector assembly of claim 18, wherein the piston further comprises the annular groove.

20. The injector assembly of claim 18, wherein the at least one roller retainer is adapted to hold the at least one roller in the annular groove.

21. The injector assembly of claim 18, wherein the pneumatic pressure unit comprises an exhaust assembly adapted to release compressed air from the pneumatic pressure unit.

22. The injector assembly of claim 21, wherein the exhaust assembly comprises a channel, at least one gasket, and at least one orifice plate.

23. The injector assembly of claim 18, wherein the first component further comprises a protective cap.

24. The injector assembly of claim 18, wherein the first component further comprises a dosing unit configured to adjust the delivery of a predetermined amount of a substance.

25. The injector assembly of claim 18, wherein the predetermined amount of pressure is at least approximately 70% of the operation pressure of a compressed gas.

26. A method of preventing premature injection of a substance from an injector assembly, comprising:
 (a) locking a driving assembly into a lock assembly;
 (b) increasing pressure from a pneumatic power unit against the driving assembly;
 (c) retaining the driving assembly in the lock assembly until a predetermined amount of pressure from the pneumatic power unit builds against the driving assembly; and
 (d) overcoming with the predetermined amount of pressure an opposing force created by the driving assembly.

27. The method of claim 26, further comprising releasing the driving assembly from the lock assembly once the predetermined amount of pressure has been built against the driving assembly.

28. The method of claim 27, further comprising relocking the driving assembly into the lock assembly.

29. The method of claim 28, wherein relocking the driving assembly into the lock assembly comprises: (a) supplying the pressure to the driving assembly; (b) overcoming the opposing force created by the driving assembly; and (c) realigning the driving assembly into the lock assembly.

30. The method of claim 28, wherein relocking the driving assembly into the lock assembly further comprises the step of drawing the substance into the injector assembly.

31. The method of claim 26, further comprising drawing a substance into the injector assembly.

32. The method of claim 26, wherein increasing pressure against the driving assembly comprises supplying a compressed gas to a cavity near the driving assembly.

33. The method of claim 26, wherein supplying a compressed gas to the cavity near the driving assembly comprises triggering a release of the compressed gas from the pneumatic power unit, the pneumatic power unit communicating with the cavity near the driving assembly.

34. The method of claim 26, further comprising changing the dosage amount of the substance in the injector assembly.

35. The method of claim 26, wherein the predetermined amount of pressure is derived from a compressed gas having an operation pressure of at least approximately 70%.

36. The method of claim 26, further comprising relocking the driving assembly into the lock assembly, wherein relocking the driving assembly into the lock assembly comprises: (a) supplying a pressure to the driving assembly; (b) overcoming an opposing force created by the driving assembly; and (c) realigning the driving assembly into the lock assembly.

* * * * *